(12) United States Patent
Moore et al.

(10) Patent No.: US 9,439,787 B2
(45) Date of Patent: Sep. 13, 2016

(54) METHOD OF COATING A STENT

(71) Applicant: Cook Medical Technologies LLC, Bloomington, IN (US)

(72) Inventors: William F. Moore, Bloomington, IN (US); Nathan S. Ridgley, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 648 days.

(21) Appl. No.: 13/798,885

(22) Filed: Mar. 13, 2013

(65) Prior Publication Data

US 2014/0102598 A1 Apr. 17, 2014

Related U.S. Application Data

(60) Provisional application No. 61/713,925, filed on Oct. 15, 2012.

(51) Int. Cl.
| | | |
|---|---|---|
| A61F 2/82 | (2013.01) | |
| C22F 1/00 | (2006.01) | |
| C22F 1/10 | (2006.01) | |
| C22F 1/18 | (2006.01) | |
| A61F 2/91 | (2013.01) | |
| A61F 2/95 | (2013.01) | |

(52) U.S. Cl.
CPC . *A61F 2/82* (2013.01); *A61F 2/91* (2013.01); *A61F 2002/9522* (2013.01); *A61F 2240/001* (2013.01); *A61F 2250/0067* (2013.01)

(58) Field of Classification Search
CPC ............ C22F 1/006; A61F 2/82; A61F 2/91; A61F 2002/9522; A61F 2240/001; A61F 2250/0067

USPC ......................................................... 148/563
See application file for complete search history.

(56) References Cited

U.S. PATENT DOCUMENTS

| | | | |
|---|---|---|---|
| 6,241,691 B1 | 6/2001 | Ferrera et al. | |
| 6,607,553 B1 | 8/2003 | Healy et al. | |
| 6,921,441 B2 * | 7/2005 | Tanaka et al. | ................ 148/421 |
| 7,323,189 B2 | 1/2008 | Pathak | |
| 8,101,275 B2 | 1/2012 | Schüssler et al. | |
| 8,187,396 B2 | 5/2012 | Parker | |
| 2004/0193257 A1 | 9/2004 | Wu et al. | |

(Continued)

FOREIGN PATENT DOCUMENTS

EP 0 362 444 A1 10/1988

OTHER PUBLICATIONS

Kim, H. Y., et al. "Martensitic transformation, shape memory effect and superelasticity of Ti—Nb binary alloys." Acta Materialia 54.9 (2006): 2419-2429.*

(Continued)

*Primary Examiner* — Jessee Roe
(74) *Attorney, Agent, or Firm* — Brinks Gilson & Lione

(57) ABSTRACT

A method of coating a stent is provided that minimizes damage to the coating. The stent is self-expanding and made of a superelastic material. The stent is initially cooled so that at least part of the structure of the stent transforms to a martensitic phase. The stent is then compressed, coated and loaded while the structure of the stent remains at least partially martensitic. After the stent is loaded into a tubular restraint, the loaded stent is allowed to warm to room temperature.

20 Claims, 2 Drawing Sheets

(56) References Cited

U.S. PATENT DOCUMENTS

| | | |
|---|---|---|
| 2007/0184277 A1 | 8/2007 | Schüssler et al. |
| 2008/0072653 A1 | 3/2008 | Gillick et al. |
| 2008/0215131 A1* | 9/2008 | Magnuson et al. .......... 623/1.12 |
| 2009/0306767 A1 | 12/2009 | Lendlein |
| 2011/0071633 A1* | 3/2011 | Fonte .......................... 623/16.11 |
| 2014/0304877 A1* | 10/2014 | Fonte et al. ....................... 2/2.5 |

OTHER PUBLICATIONS

Extended European Search Report for 13 186 473.8 dated Jan. 3, 2014, 5 pgs.

* cited by examiner

METHOD OF COATING A STENT

This application claims priority to U.S. Provisional Application No. 61/713,925, filed Oct. 15, 2012, which is hereby incorporated by reference herein.

BACKGROUND

The present invention relates generally to coated stents and more particularly to a method for coating a superelastic self-expanding stent.

Stents are used to treat various organs, such as the vascular system, colon, biliary tract, urinary tract, esophagus, trachea and the like. For example, stents are commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

Many different types of stents and stenting procedures are possible. In general, however, stents are typically designed as tubular support structures that may be inserted percutaneously and transluminally through a body passageway. Traditionally, stents are made from a metal or other synthetic material with a series of radial openings extending through the support structure of the stent to facilitate compression and expansion of the stent. Although stents may be made from many types of materials, including non-metallic materials, common examples of metallic materials that may be used to make stents include stainless steel, nitinol, cobalt-chrome alloys, amorphous metals, tantalum, platinum, gold and titanium. Typically, stents are implanted within a passageway by positioning the stent within the area to be treated and then expanding the stent from a compressed diameter to an expanded diameter. The ability of the stent to expand from a compressed diameter makes it possible to thread the stent to the area to be treated through various narrow body passageways while the stent is in the compressed diameter. Once the stent has been positioned and expanded at the area to be treated, the tubular support structure of the stent contacts and radially supports the inner wall of the passageway. As a result, the implanted stent mechanically prevents the passageway from narrowing and keeps the passageway open to facilitate fluid flow through the passageway.

Self-expanding stents are increasingly used and accepted by physicians for treating a variety of ailments. Self-expanding stents are usually made of shape memory materials or other elastic materials that act like a spring. Typical metals used in this type of stent include nitinol and 304 stainless steel. A common procedure for implanting a self-expanding stent involves a two-step process. First, the narrowed vessel portion to be treated is dilated with a balloon but without a stent mounted on the balloon. Second, a stent is implanted into the dilated vessel portion. To facilitate stent implantation, the stent is installed on the end of an inner catheter in a compressed, small diameter state and is usually retained in the small diameter by inserting the stent into a restraining sheath at the end of the catheter. The stent is then guided to the balloon-dilated portion and is released from the inner catheter by pulling the restraining sheath away from the stent. Once released from the restraining sheath, the stent radially springs outward to an expanded diameter until the stent contacts and presses against the vessel wall. Traditionally, self-expanding stents have been more commonly used in peripheral vessels than in coronary vessels due to the shape memory characteristic of the metals that are used in these stents. One advantage of self-expanding stents for peripheral vessels is that traumas from external sources (e.g., impacts to a person's arms, legs, etc.) which are transmitted through the body's tissues to the vessel do not permanently deform the stent. Instead, the stent may temporarily deform during an unusually harsh trauma but will spring back to its expanded state once the trauma is relieved.

One type of self-expanding stent that is commonly preferred is superelastic self-expanding stents. Superelastic self-expanding stents are usually made from nitinol and remain elastic throughout an unusually large range of deformation. Thus, a superelastic self-expanding stent can have an especially large expansion ratio, which allows the stent to be compressed down to a particularly small diameter for delivery to a treatment site and yet can elastically expand sufficiently to contact and exert pressure against a vessel wall when released. This is desirable to minimize trauma during the delivery process, and also to ensure that the stent exerts a desirable level of radial force against the vessel wall once implanted.

In order to provide improved treatment results at the treatment site, some stents are coated with a drug or other type of coating. For example, a stent may be coated with a drug like paclitaxel, which is an antiproliferative that prevents renarrowing of a vessel wall. Stents may also be coated with heparin, which is an anticoagulant that prevents blood clotting. However, these are only a few examples of the types of coatings that can be applied to a stent. One problem with the use of coatings on superelastic self-expanding stents is that the coating can be damaged when the stent is compressed and loaded into the delivery system. This may be a particular problem when the coating is a drug coating since uniform distribution of the drug is typically desirable for consistent treatment results.

Accordingly, the inventors believe it would be desirable to provide an improved method for coating superelastic self-expanding stents.

SUMMARY

A method of coating a superelastic self-expanding stent is described. The stent is cooled to transform the stent structure to martensite. While the stent is cooled, the stent is compressed. After compressing, the stent is coated while remaining cooled and compressed. After coating, the stent is loaded into a tubular restraint while remaining cooled. Thereafter, the tubular restraint and stent are allowed to warm back up to room temperature. By remaining cooled during the compressing, coating and loading steps, the stent does not need to be compressed after the coating step and minimal force is required to push the stent into the tubular restraint. Thus, damage to the coating is reduced. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
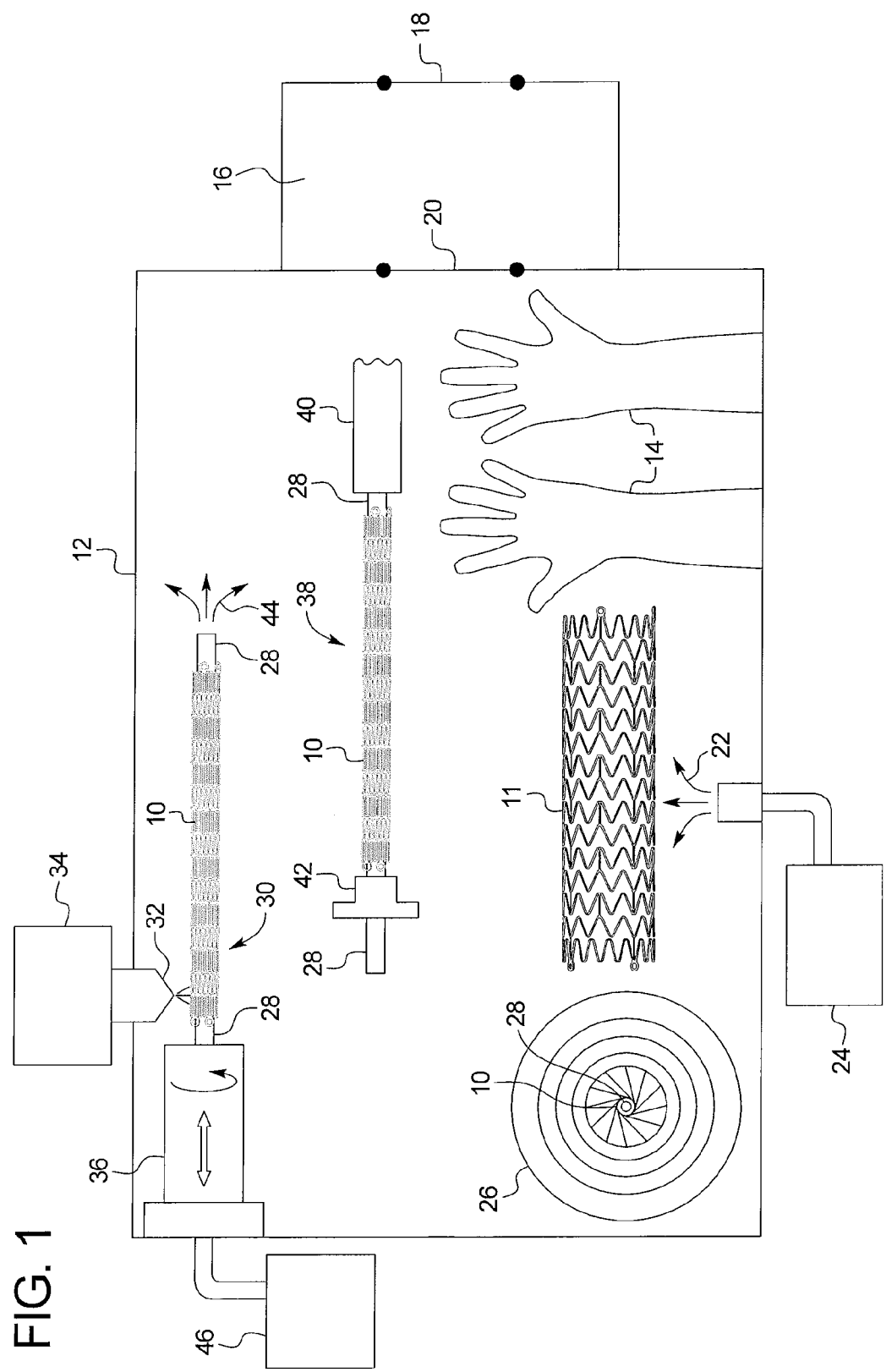
FIG. 1 is a schematic view of a cold box with a stent crimper, coating station and a loading station.
Figure 2:
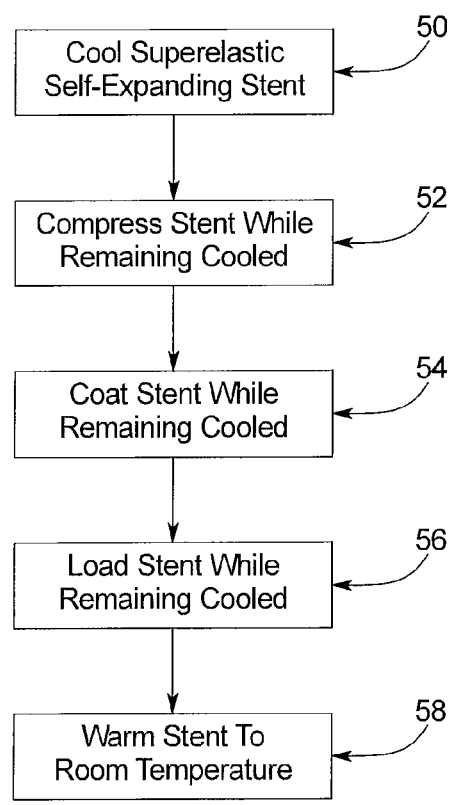
FIG. 2 is a flow chart of a method for coating and loading a stent.

Referring now to the figures, and particularly to FIG. 1, an improved method of coating and loading a superelastic self-expanding stent 10 may be carried out in a cold box 12 as shown. As those of ordinary skill in the art understand, superelastic materials like binary nitinol have metallurgical states that change in response to changes in temperature. For example, at low temperatures, nitinol transforms to a martensitic phase, and at higher temperatures transforms to an austenitic phase. More specifically, when nitinol is cooled from a higher temperature where substantially the entire structure is austenitic, the nitinol structure will begin to transform to martensite at a martensite start temperature ($M_s$). As the nitinol structure is cooled further, substantially the entire structure becomes martensitic at a martensite finish temperature ($M_f$). Thereafter, when the nitinol structure is warmed, the structure will begin to transform to austenite at an austenite start temperature ($A_s$), which is typically higher than the $M_f$ temperature and the $M_s$ temperature. As the nitinol structure is warmed further, substantially the entire structure becomes austenitic at an austenite finish temperature ($A_f$).

In the simplest form of the invention, the cold box 12 may be a single enclosed chamber where the ambient temperature in the cold box 12 is maintained below the $M_f$ temperature of the superelastic self-expanding stent 10 to be coated and loaded. For example, it may be desirable to maintain the temperature within the cold box 12 below about −40° C. The cold box 12 may be provided with sealed glove openings 14 to allow an operator to access the interior of cold box 12, and the cold box 12 may be provided with a transfer chamber 16 with an outer and inner door 18, 20 to move the stent 10 and other components in and out of the cold box 12 without significantly impacting the controlled temperature in the cold box 12. The temperature in the cold box 12 may be cooled with nitrogen gas 22 that is blown into the cold box 12 from a nitrogen reservoir 24. However, other methods of cooling may also be used, such as a heat exchanger system if desired.

Once the stent 10 is placed in the cold box 12, the stent 10 is preferably cooled below the $M_f$ temperature of the superelastic material used in the stent 10 so that the structure of the stent 10 becomes substantially completely martensitic (50). This may be done in the cold box 12 by allowing an expanded stent 11 to rest for a period of time in the cold box 12 to allow the ambient temperature to cool the stent 10. The stent 10 could also be dipped in liquid nitrogen to cool the stent 10. Once cooled, the operator may use the sealed gloves 14 to place the stent 10 in a stent crimper 26 and operate the stent crimper 26 to collapse the stent 10 down to a small diameter compressed state (52). Any type of conventional stent crimper 26 may be used, such as an iris type crimper 26. The stent 10 may also be crimped in a cigarette-like roller with a metal foil or in any other suitable manner. Preferably, the stent 10 is compressed onto a mandrel 28 to facilitate moving the stent 10 within the cold box 12. Since the structure of the stent 10 remains martensitic after the stent 10 is compressed because the stent 10 remains cooled, the stent 10 does not self-expand to its larger, expanded diameter as it would if the structure were austenitic.

While the stent 10 is cooled and in the compressed state, the stent 10 is moved on the mandrel 28 in the cold box 12 to a coating station 30, where a coating is applied to the outer surface of the stent 10 (54). Various types of coating methods may be used, such as electrostatic spray, atomized spray and dip coating. However, a particularly preferred coating method is ultrasonic spray deposition. In ultrasonic spray deposition, an ultrasonic wave is used to break up the coating fluid into small particles. A carrier gas then picks up the coating particles and is forced through a nozzle 32 toward the stent 10. Ultrasonic spray deposition may be desirable since less overspray is needed, less solvent may be needed, and less exhaust may be required. The spray nozzle 32 is preferably stationary, and the coating reservoir 34 may be located outside of the cold box 12. In order to move the stent 10 longitudinally and rotationally past the spray nozzle 32, the mandrel 28 may be mounted on a motorized fixture 36. Although numerous types of coatings may be applied to the outer surface of the stent 10, drug coatings like paclitaxel are preferred.

After the stent 10 is coated, the stent 10 and mandrel 28 may be moved from the coating station 30 to a loading station 38. In the loading station 38, the stent 10 may be slid off the mandrel 28 into the restraining sheath 40 of a delivery system (56). A pusher 42 may be provided that slides over the mandrel 28 to push the stent 10 into the restraining sheath 40. Since the structure of the stent 10 remains in the martensitic state, minimal force will typically be needed to slide the stent 10 into the restraining sheath 40.

After the stent 10 is loaded into the restraining sheath 40, the restraining sheath 40 and loaded stent 10 may be removed from the cold box 12 and allowed to warm back up to room temperature (58). This causes the stent structure to transform to austenite. As a result, when the stent 10 is later released from the restraining sheath 40 during treatment of a patient, the stent 10 will self-expand toward its larger diameter expanded state. However, because the stent 10 was coated and loaded while in the martensitic state, minimal stresses are applied to the coating to reduce the potential for damaging the coating.

Although in the preferred method described above the stent 10 is cooled in a cold box 12 and maintained below $M_f$ during the compressing, coating and loading steps, variations on the preferred method may be made while minimizing damage that may occur to the coating. For example, the stent 10 may be cooled below $M_s$ to transform at least some of the stent structure to martensite, while maintaining the stent 10 below $A_f$ during compression, coating and loading to ensure that the structure of the stent 10 does not transform substantially completely to austenite. It is also preferable that the stent 10 remain below $A_s$ during compression, coating and loading so that none of the martensitic structure transforms to austenite until after the stent 10 is loaded. Thus, it may be possible for the stent 10 to warm slightly after the cooling step as long as the stent 10 remains below $A_f$, and preferably, $A_s$.

The method may also be performed in an enclosed chamber other than a cold box 12 or the stent 10 may be cooled and maintained in a cooled state without an enclosed chamber during the entire method. For example, the stent 10 may be cooled in the crimper 26 and then transferred to the coating station 30 before the stent 10 has time to warm up significantly. In order to maintain the stent 10 in a cooled state, the stent 10 may be dipped in liquid nitrogen as necessary. Once loaded in the coating station, nitrogen gas 44 from a reservoir 46 may be pumped through a hollow mandrel 28 upon which the stent 10 is mounted to maintain the stent 10 in a cooled state during coating. As a result, the surrounding ambient temperature need not be maintained at as low a temperature since the nitrogen gas 44 flowing through the mandrel 28 may keep the stent 10 cool despite a higher ambient temperature.

The stent 10 may also be loaded into a tubular restraint other then the restraining sheath 40 in a delivery system. For example, the stent 10 may be loaded into a PTFE transfer tube. Subsequently, the stent 10 may then be pushed out of the transfer tube and pushed into the restraining sheath 40 of a delivery system, either at room temperature or at a cooled temperature when the stent 10 is partially or fully martensitic.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A method of coating and loading a superelastic self-expanding stent, comprising:
cooling a stent below a martensite start temperature, said stent being self-expanding and being made of a superelastic nickel-titanium memory shape metal material having a martensitic phase and an austenitic phase; compressing said stent after said cooling step while said stent remains below an austenite finish temperature; coating said stent with a drug to form a drug-coated stent after said compressing step while said stent remains below said austenite finish temperature; loading said drug-coated stent in a compressed state within a tubular restraint after said coating step while said drug-coated stent remains below said austenite finish temperature; and warming said stent within said tubular restraint after said loading step.

2. The method according to claim 1, wherein said stent remains below an austenite start temperature during said compressing, coating and loading steps.

3. The method according to claim 1, wherein said stent is cooled below a martensite finish temperature during said cooling step.

4. The method according to claim 3, wherein said stent remains below an austenite start temperature during said compressing, coating and loading steps.

5. The method according to claim 4, wherein said stent remains below a martensite finish temperature during said compressing, coating and loading steps.

6. The method according to claim 5, wherein said stent is cooled below about −40° C. during said cooling step and said stent remains below about −40° C. during said compressing, coating and loading steps.

7. The method according to claim 1, wherein said cooling, compressing, coating and loading steps occur within an enclosed chamber, an ambient temperature within said enclosed chamber remaining below said martensite start temperature.

8. The method according to claim 1, wherein said cooling, compressing, coating and loading steps occur within an enclosed chamber, an ambient temperature within said enclosed chamber remaining below a martensite finish temperature.

9. The method according to claim 8, wherein said enclosed chamber comprises a single chamber with sealed glove openings, an operator thereby being able to access said stent within said enclosed chamber to compress, coat and load said stent.

10. The method according to claim 1, wherein said coating is applied to an outer surface of said stent.

11. The method according to claim 1, wherein said coating step comprises ultrasonic spray deposition.

12. The method according to claim 1, wherein said stent is compressed onto a mandrel in a crimper during said compressing step, said mandrel and said stent are transferred to a coating station after said compressing step, and said stent is transferred from said mandrel into said tubular restraint after said coating step.

13. The method according to claim 1, wherein said tubular restraint is a restraining sheath of a delivery system for said stent.

14. The method of claim 1, wherein said drug is selected from the group consisting of an antiproliferative and an anticoagulant.

15. The method according to claim 1, wherein said stent remains below an austenite start temperature during said compressing, coating and loading steps, and said coating is applied to an outer surface of said stent.

16. The method according to claim 15, wherein said tubular restraint is a restraining sheath of a delivery system for said stent.

17. The method according to claim 16, wherein said stent is cooled below a martensite finish temperature during said cooling step, and said stent remains below a martensite finish temperature during said compressing, coating and loading steps.

18. The method according to claim 17, wherein said cooling, compressing, coating and loading steps occur within an enclosed chamber, an ambient temperature within said enclosed chamber remaining below a martensite finish temperature.

19. The method according to claim 18, wherein said enclosed chamber comprises a single chamber with sealed glove openings, an operator thereby being able to access said stent within said enclosed chamber to compress, coat and load said stent.

20. The method according to claim 17, wherein said cooling, compressing, coating and loading steps occur within an enclosed chamber, an ambient temperature within said enclosed chamber remaining below a martensite finish temperature, and said stent is compressed onto a mandrel in a crimper during said compressing step, said mandrel and said stent are transferred to a coating station after said compressing step, and said stent is transferred from said mandrel into said restraining sheath after said coating step.

* * * * *